United States Patent [19]

Stoner

[11] Patent Number: 5,244,096
[45] Date of Patent: * Sep. 14, 1993

[54] PREVENTIVE TREATMENT KIT AGAINST SEXUALLY TRANSMITTED DISEASE

[76] Inventor: Fred L. Stoner, 500 S. Rancho Dr., Unit A-1, Las Vegas, Nev. 89106

[*] Notice: The portion of the term of this patent subsequent to May 15, 2007 has been disclaimed.

[21] Appl. No.: 934,359

[22] Filed: Aug. 20, 1992

Related U.S. Application Data

[63] Continuation-in-part of Ser. No. 719,185, Jun. 21, 1991, abandoned, which is a continuation-in-part of Ser. No. 184,842, Apr. 22, 1988, abandoned.

[51] Int. Cl.$^5$ .............................................. B65D 71/00
[52] U.S. Cl. ...................................... 206/581; 206/69; 206/570; 206/209
[58] Field of Search ................. 206/69, 209, 223, 232, 206/570, 581; 514/705, 698

[56] References Cited

U.S. PATENT DOCUMENTS

| | | | |
|---|---|---|---|
| 3,608,086 | 9/1971 | Halpern | 514/557 |
| 4,678,664 | 7/1987 | Schmolka | 424/642 |
| 4,898,859 | 2/1990 | Fuji et al. | 514/210 |
| 4,925,033 | 5/1990 | Stoner | 206/581 |
| 5,001,143 | 3/1991 | Hokazono et al. | 514/430 |
| 5,037,976 | 8/1991 | Fuji et al. | 540/300 |
| 5,124,359 | 6/1992 | Wachman et al. | 514/705 |

OTHER PUBLICATIONS

Mary Harbison and Scott Hammes "Inactivation of HIV" Journal of Acquired Immune Deficiency Syndrome, vol. 2, No. 1 1989.

Primary Examiner—David T. Fidei
Attorney, Agent, or Firm—Henri J. A. Charmasson

[57] ABSTRACT

A method and kit which combines a condom, cleaning implements such as a toothbrush, and a plurality of solutions containing povidone-iodine complex; a before-contact mouth solution, a before-contact body solution, an after-contact mouth solution, and an after-contact body solution. Up to 3 hours before sexual contact, the condoom is applied and exposed skin and condom areas are cleansed with the before-contact solutions an cleaning implements. This includes: hands, mouth, genitals, lower abdomen, upper thighs and rectum. The solutions also produce a coating action that functions as a sustained chemical barrier and a coating which covers minor cuts or abraded areas before sexual contact. During sexual contact, the coating also acts as a lubricant, reducing further abrasions. After sexual contact, the after-contact solutions and cleaning implements are used to cleanse the exposed or potentially contaminated areas and the condom is removed. The solutions further reduce microbial activity and once again coat and heal any abraded areas. The before and after solutions contain at least 0.25 percent by weight of povidone-iodine with the remainder primarily water. The mouth solution may include chlorhexidine gluconate, sodium propionate, chlorophyllin copper complex, or as an alternate microbicidal agent. Both types of solutions are non-staining, water soluble and can be pleasantly flavored and/or scented for ease of use and sensory pleasure.

8 Claims, 5 Drawing Sheets

PREVENTIVE TREATMENT KIT AGAINST SEXUALLY TRANSMITTED DISEASE

PRIOR APPLICATIONS

This application is a continuation-in-part of Ser. No. 07/719,185 filed Jun. 21, 1991, a continuation of Ser. No. 07/184,842 filed Apr. 22, 1988 now both abandoned.

FIELD OF THE INVENTION

This invention relates to combinations of drugs, germicides, cleansers, and microbicidal barriers, and to methods of preventing the transmission of sexually transmitted diseases using a combination of these articles, more specifically to a method of preventing the transmission of Acquired Immune Deficiency Syndrome (AIDS) plus other sexually transmitted diseases.

BACKGROUND OF THE INVENTION

Sexually transmitted diseases (STD) can be defined as diseases that can be transmitted from one person to another primarily during sexual intercourse activities and body contacts between an infected individual and an uninfected individual. There are currently over twenty-six (26) recognized STD's, including AIDS, Syphillis, Gonorrhea and Herpes. The contact sites believed to be the most responsible for STD transmission are the genitals, rectum, mouth and hands. Because of the variety of sexual and related contacts between these contact sites, no single treatment of a single site is known to be fully effective in preventing the transmission of STD's.

A combination of microbicidal agents, cleansing agents and barriers for preventing the transmission of sexually transmitted diseases should be easy to use, reliable, pleasing to the senses and low in cost. More importantly, the materials and method must have a high effectiveness in preventing AIDS and other sexually transmitted diseases in a real life sexual encounter, not only in a laboratory environment.

Current devices and methods to prevent the transmission of AIDS and other venereal diseases tend to fall into three categories. The first is a solid barrier, such as a condom or diaphragm or vaginal sponge, which attempts to prevent a portion of one partner's skin and body fluids from contact with the other partner's skin or body fluids. The second method is a chemoprophylaxis or antibiotic injection or oral administration, which attempts to suppress the activity of the microbial agents that enter the body and cause the sexually transmitted diseases. The final method is the use of coating fluids (foams, creams, jellies) on affected portions, which form a viscous barrier to microbes and reduce abrasion. Some combinations of these three basic methods are known, as well as in combination with other treatment objectives, for example, birth control foams combined with spermicide compounds, such as nonoxynol-9, that also act as anti-microbial agents.

These prior approaches have many limitations, primarily related to the uncontrolled variety of body and fluid contact sites before, during and after sexual activity, and the multiplicity of microbial agents involved. Although the first (barrier) method, if used properly, can significantly reduce the incidence of sexually transmitted diseases, it may increase irritation, allergic reactions, and introduce additional microbes. Since it is believed that at least some of the sexually transmitted diseases can only be transmitted through a break in the skin, these side effects might actually cause transmission of a disease which would otherwise not be transmitted.

Other limitations are also that the barrier does not protect uncovered portions at or near the genitals, such as the testicles or rectal area, or non-genital areas, such as the mouth and hands. These uncovered portions are also frequently in contact with the sexual partner or fluids from the sexual partner. In addition, placement and especially removal of a contaminated barrier can also transmit disease. Solid barriers have also been used in combination with anti-microbial agents and coating fluids. although improved protection resulted, the microbial agent caused added irritations, allergies and candidiasis infections in many users. In addition, this combined method still did not address some of the limitations previously noted, such as before and after contacts with exposed/contaminated but unprotected including: the mouth; hands; and paragenital areas.

Studies conducted on the effectiveness of various antimicrobial agents placed in the genital areas (the second method) in preventing sexually transmitted diseases, including: triethanolanime in oil, mapharsen and sodium alurel have shown a decrease in the rates of some sexually transmitted diseases, but increases in the rates of non-gonoccal urethritis, candidasis, anti-microbial resistances, and allergic reactions. Vaginal drying has also been noted in other studies. It was recognized that finding an antibiotic that can be totally effective against the variety of microbial agents involved in sexually transmitted diseases, 1) without side effects of repeated use and 2) in the variety of human contacts involved in sexual encounters would be unlikely, if not impossible, and recent research has concentrated in other areas. Many of the limitations previously discussed were also present, such as the protection of non-genital surfaces.

Tests of the third method using a coating fluid, especially in conjunction with a spermicide and antimicrobial properties as well, have again shown decreased incidence in some sexually transmitted diseases, but significant side effects (irritations, allergies, vaginal drying, and infections) were again observed.

None of the prior art known to the applicant incorporates treatment and protection of all of the paragenital and non-genital areas that may be involved during a sexual encounter. None of the prior art known to the applicant uses a mild, previously non-specific anti-microbial agent with no known side effects and derived from a natural element, either alone or in conjunction with barriers and/or viscous fluids. None of the prior art known to the applicant provides a combination of articles to be applied to all of the paragenital and non-genital areas to prevent the transmission of STD's. Although rinsing and douche of the genitals is known, none of the prior methods for preventing sexually transmitted diseases known to the applicant incorporate a douche and/or cleansing of all the affected areas. Although other antiseptic mouthwashes have been long known and used for therapeutic purposes, no prior method known to the applicant uses a mouthwash for preventing sexually transmitted diseases.

In view of the rapid spread of the AIDS epidemic, what is urgently needed is a simple combination of devices and a method of prevention using these devices which does not require the use of costly pharmacopia and does not interfere with the enjoyment of the sexual encounter. It would also be beneficial to present these devices in a convenient package grouping all the elements necessary to quickly and effectively practice the preventive method.

SUMMARY OF THE INVENTION

The principal and secondary objects of the invention are:

To provide a safe and effective application of a combination of cleansing agent, microbicidal agent and barrier in a method applying these devices to prevent the transmission of sexually transmitted diseases, including AIDS;

To essentially eliminate significant side effects from prevention method and associated combination of devices;

To provide a kit containing the devices and instructions on the prevention method which is easy and pleasant to use and may be used in conjunction with birth control or other materials and/or methods; and To provide said kit in a compact package that can be sold over the counter in convenience stores or from automatic vending machines for widespread and low-cost availability.

These and other objects are achieved by a method and kit which combines a condom, at least one cleaning implement, and a plurality of coating and antimicrobicidal solutions containing povidone-iodine complex. The solutions include a before-contact mouth solution, a before-contact body solution, an after-contact mouth solution, and an after-contact body solution. Up to three hours before sexual contact, the solution is applied over the exposed areas of skin and areas are cleansed with the before-contact solutions and cleaning implements, such as a toothbrush for cleaning the mouth. This includes: hands, mouth, genitals, lower abdomen, upper thighs and rectum. The solutions also produce a coating action that functions as sustained chemical barrier and a coating which covers minor cuts or abraded areas before sexual contact. During sexual contact, the coatings also act as a lubricant, reducing further abrasion. After sexual contact, the after-contact solutions and cleaning implements are used to cleanse the exposed or potentially contaminated areas and the condom is removed. The solutions further reduce microbial activity and once again coat and heal any abraded areas. The mouth solutions may be in the form of toothpaste and or gargle and contain at least 0.25 percent by weight of povidone-iodine or other equivalent microbicidal element with the remainder primarily water. both types of solutions are non-staining, water soluble and can be pleasantly flavored and scented for ease of use and sensory pleasure. Cleaning implements can include toothbrush, wash cloths and brushes. In the preferred embodiments of the invention the kit is boxed in a cigarette-pack sized box for convenient dispensing from cigarette or candy vending machines.

DESCRIPTION OF THE PREFERRED EMBODIMENTS OF THE INVENTION

Figure 1:
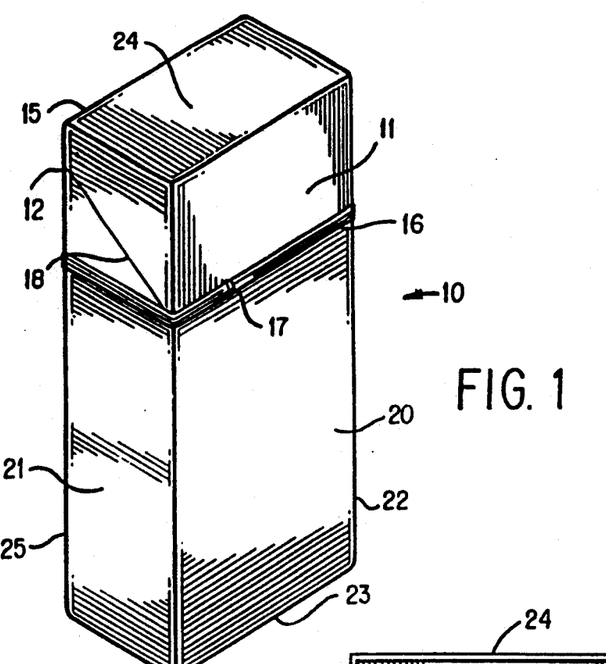
FIG. 1 shows a perspective view of a single use prevention kit enclosure.

FIG. 1 shows a side perspective view of a single use prevention kit enclosure. A cigarette-type of flip up box 10 is used to package the elements of the preferred embodiment of the prevention kit. The box 10 is composed of a lid 11, a lid joint or box handle 12, an interior space in the box for storing the elements of the kit (item 13 shown in FIG. 4), a transparent foil or cellophane seal or wrapping 15, a tap strip 16 for opening of the cellophane 15 of box 10, a tab or means for beginning to opening 16 the cellophane 15, box edges matching lid 11 (left matching edge 18 and right matching 19 shown in FIG. 3), a front of box 20, a left side 21 of box 20, a right side 22 of box 20, a bottom 23 of box 20, a top 24 of box lid 11, and a back 25 of box 20 (shown in FIG. 2). The overall size, shape and configuration is selected to fit into cigarette vending machines or similar dispensing apparatus.

Figure 2:
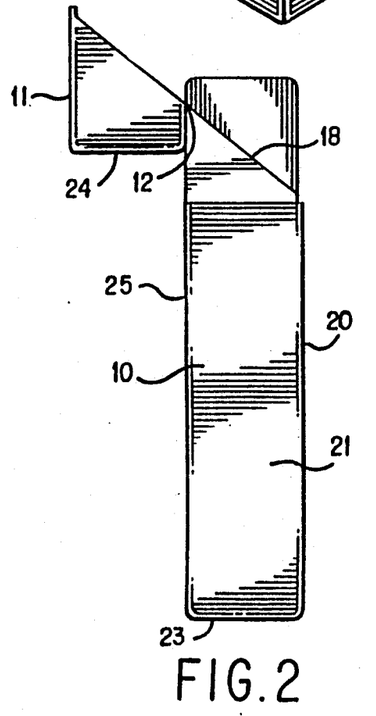
FIG. 2 shows a side view thereof with open cover.

FIG. 2 shows a left side view of a single use prevention kit box 10 having the lid 11 open. The lid 11 and top 24 folds on joint 12 to back 25. Left side matching edge 18 is now exposed along with the elements contained in the box 10. The front 20, bottom 23 and left side 21 form the remainder of the box 10 visible from this view.

Figure 3:
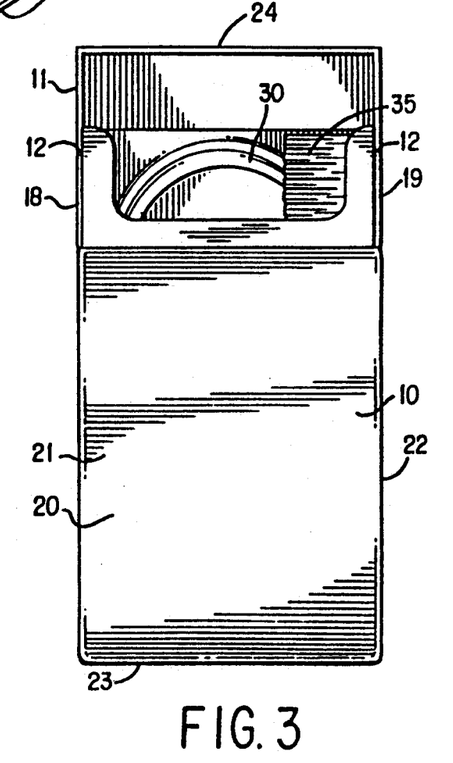
FIG. 3 shows a front view thereof.

FIG. 3 shows a front view of a single use prevention kit box 10 having the lid 11 open exposing the contents or elements of the prevention kit. The elements consist of condom package 30, a folded instruction sheet 31 (see FIG. 4), a tooth brush 35, and four containers of solutions (see FIG. 4) including tear-off tops (34) of a before-contact oral solution (36), an after-contact oral solution (37), a before-contact body solution (38), and an after-contact body solution (39). These elements are protected and contained by lid top 24, lid 11 and lid hinge 12, left side matching edge 18, right side matching edge 19, left side 21, right side 22, front 20 and bottom 23.

Figure 4:
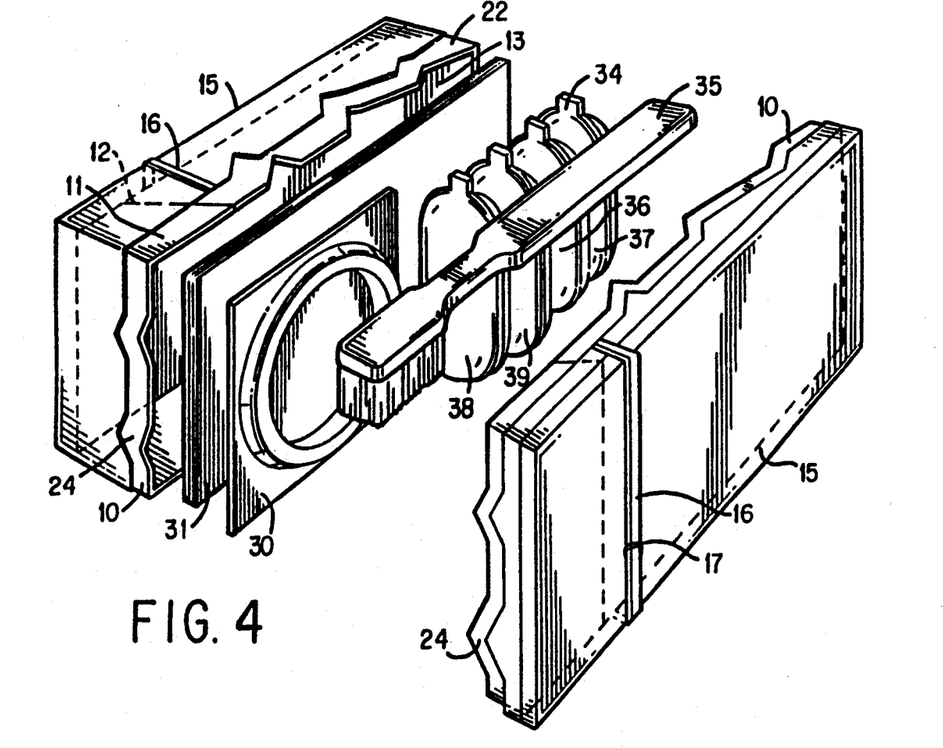
FIG. 4 shows an exploded view of a single use prevention kit enclosure and contents.

FIG. 4 shows an exploded view of a single use prevention kit. Box 10 encloses a single condom package 30, sheet of instructions 31, single use containers having tear-off tops 34 of before-contact oral solution 36, after-contact oral solution 37, before-contact body solution 38 and after-contact body solution 39. Access to the contents of the box is provided by a tab 17 opening the tab strip 17, allows one to open lid 11 and top 24 along hinge 12. The interior 13 of box 10 is formed by the right side 22 and remained side, back, front and bottom of box 10.

Figure 5:
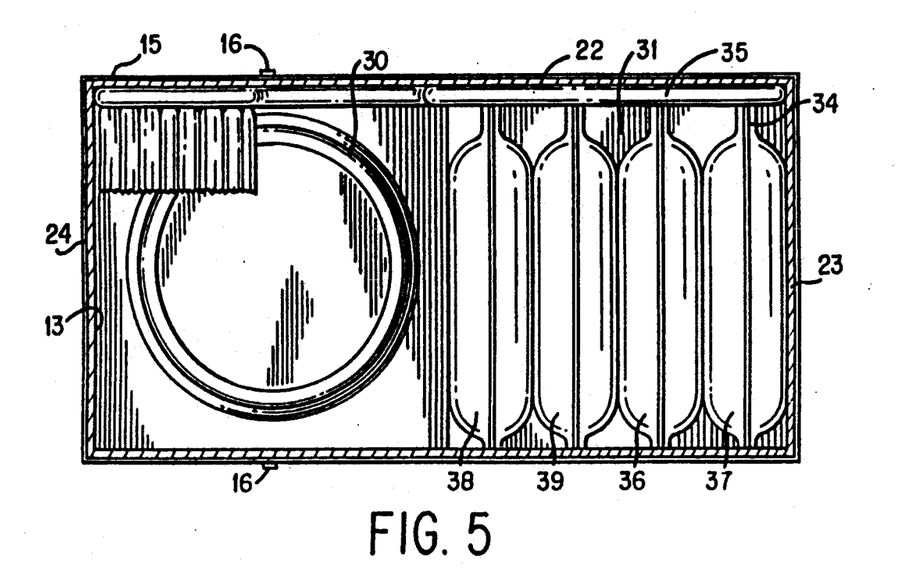
FIG. 5 shows a front cross-sectional view thereof.

FIG. 5 shows a front cross-sectional view of a single use prevention kit lying on one side. The four single use containers, 36, 37, 38, 39 are composed of half shell plastic moldings joined to have ported neck 34. Breaking the neck seal of these single use disposable containers allows the generally liquid solution to be poured or squeezed out of the containers. Containers would be individually labeled and/or color coded. In the preferred embodiment, the containers are of equal size. The same solution fills the before-contact oral and after-contact oral containers. Similarly, another solution fills both the before-contact body and after-contact body containers. However, other embodiments could have unequal sized containers and various solutions of povidone-iodine. The preferred embodiment places the containers on one side of the condom package and toothbrush, but alternate placements are also possible. The contents are again contained in the interior 13 by bottom 23, right side 22, top 24, cellophane 15 and tab strip 16.

Figure 6:
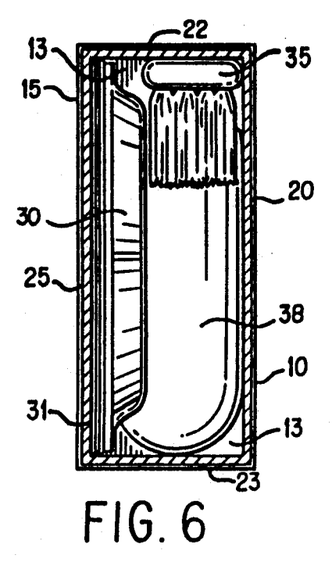
FIG. 6 shows a left side cross-sectional view thereof.

FIG. 6 shows a left side cross-sectional view of a single use prevention kit lying on its sides as viewed from the left side of the view shown in FIG. 5. The edge view of the instruction sheet 31 is adjacent to condom package 30, which is adjacent to the toothbrush 35, which partially obscures one of the containers 38 (other containers not visible in this view). The contents of the interior 13 of box 10 are again contained by front 20, bottom 23, right side 22, back 25, and cellophane 15.

Figure 7:
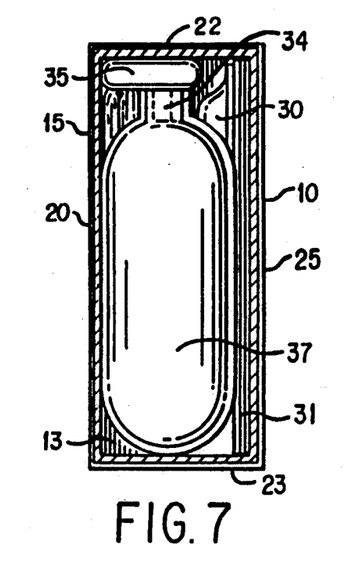
FIG. 7 shows a right side cross-sectional view thereof.

FIG. 7 shows a right side cross-sectional view of a single use prevention kit. A full side view of one of the containers 37 adjacent to the sheet of instructions 31 partially obscures the toothbrush 35 and condom package 30 in box 10. The contents of the interior 13 of box 10 are again contained by front 20, bottom 23, right side 22, back 25, and cellophane 15.

Figure 8:
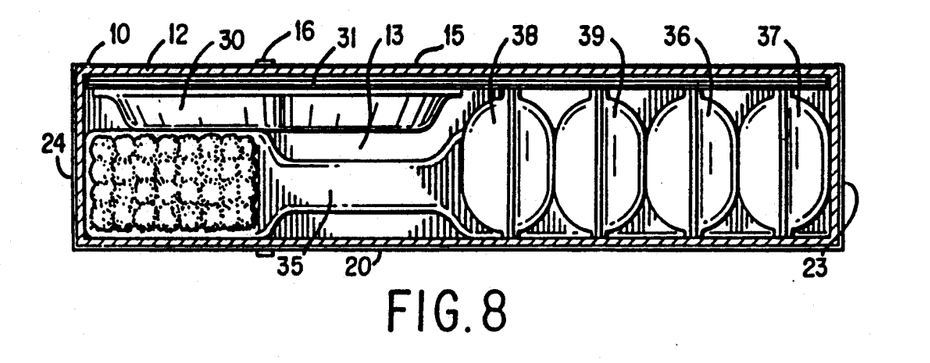
FIG. 8 shows a top cross-sectional view thereof.

FIG. 8 shows a bottom cross-sectional view of a single use prevention kit. The sheet of instructions again lies adjacent to condom package 30, which lies adjacent to toothbrush 35 which is partially obscured by the four containers 36, 37, 38, 39 in the interior 13 of box 10. The contents of the interior 13 of box 10 are again contained by front 20, bottom 23, top 24 joined at hinge 12, and cellophane 15, tab strip 16.

Figure 9:
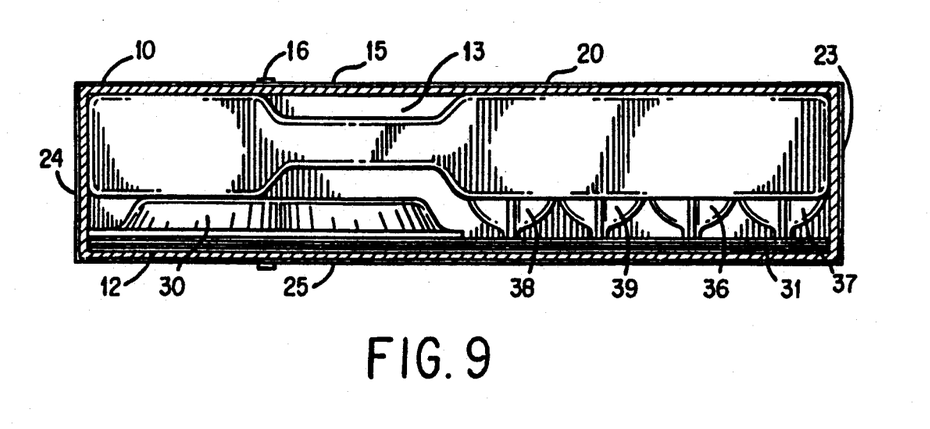
FIG. 9 shows a bottom cross-sectional view thereof.

FIG. 9 shows a top cross-sectional view of a single use prevention kit. The sheet of instructions again lies adjacent to condom package 30, which lies adjacent to toothbrush 35 which is partially obscured by the four containers 36, 37, 38, 39 in the interior 13 of box 10. The contents of the interior 13 of box 10 are again contained by front 20, bottom 23, right side 20, left side 21, top 24 joined at hinge 12, and cellophane 15, tab strip 16.

Figure 10:
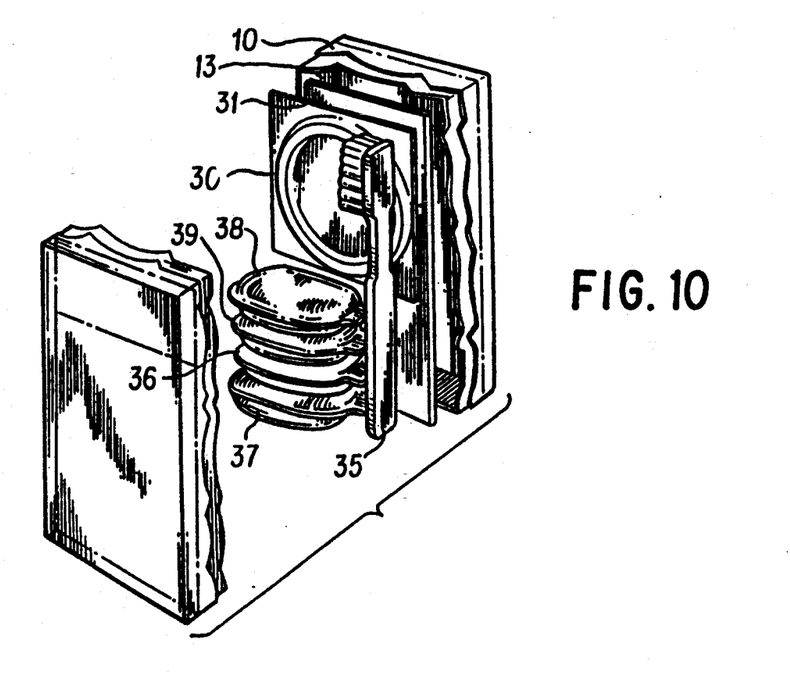
FIG. 10 shows an exploded side perspective view of a single use prevention kit enclosure and contents.

FIG. 10 shows an exploded side perspective view of a single use prevention kit. The interior 13 of box 10 may be separate padded insert to protect the contents and devices contained in the kit. The devices are a disposable toothbrush 35, two disposable containers of oral solution 36, 37, two disposable containers of body solution 38, 39, and a sheet of instructions 31.

Figure 11:
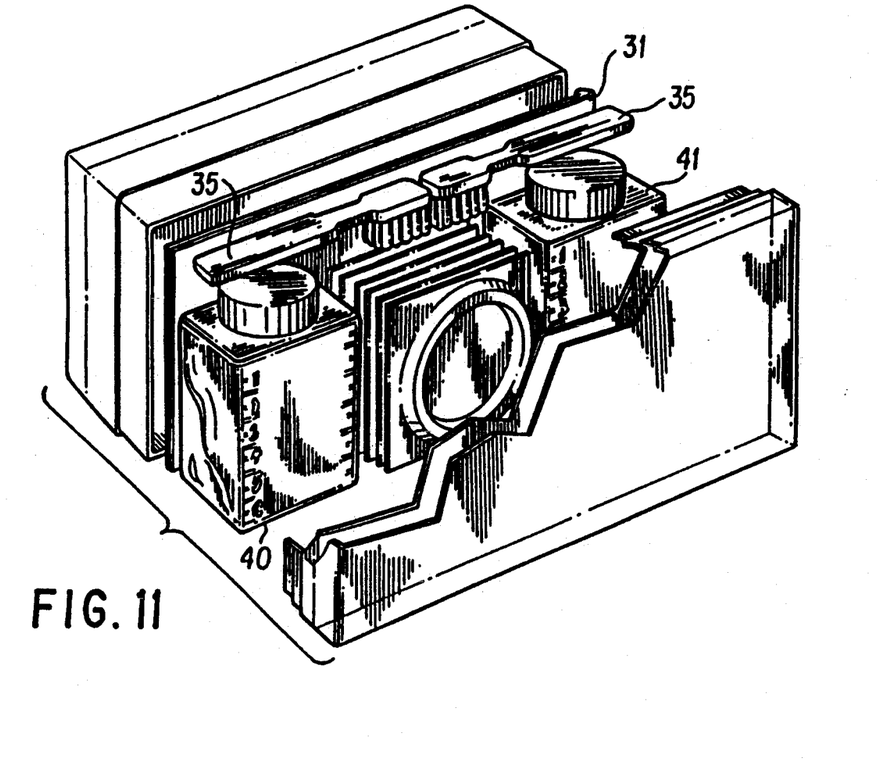
FIG. 11 shows an exploded side view perspective view of a multiple use pack.

FIG. 11 shows an exploded side perspective view of a multiple use pack. Multiple toothbrushes 35 are provided with multiple condom packages. The oral solution in container 40 is a mouthwash and body solution, in container 41 is a liquid soap. Multiple use containers hold sufficient amounts for multiple applications of the solutions. The sheet of instructions 31 would contain the specific amounts of solutions to be used for before and after-contact uses, such as a capful. Multiple use packages could be provided for a single use by both sexual partners or a plurality of uses by a single user.

Figure 12:
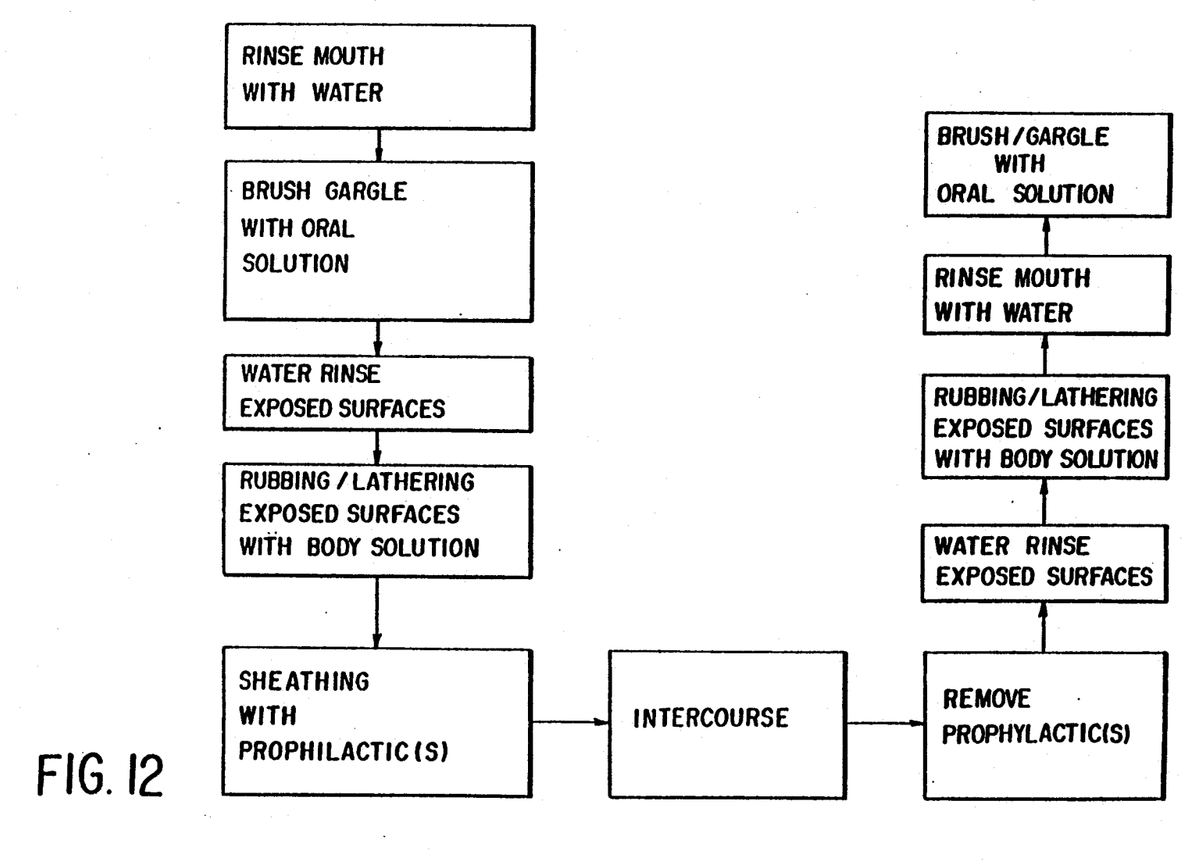
FIG. 12 shows a block diagram of a preventive method.

FIG. 12 shows a block diagram of a preventive method of using the preferred embodiment. The initial step is to rinse the mouth with water, followed by brushing with a portion of the before-contact oral solution, followed by a gargle of the remaining solution used as a mouthwash. An alternative would be to package the before-contact solution in two packages, one having the consistency of a toothpaste, the other having the consistency of a mouthwash. The brushing and gargling can be followed by a second rinse with water. The first rinse, brushing, gargling and second rinse cleanses the mouth of foods and residue that may act as a growth media for STD microbes and coats the mouth acting as a broad, nonspecific anti-microbial agent plus a coating action over minor cuts or sores. An alternate, but less effective method is to delete the initial water rinse, relying upon brushing or gargling with the oral solution to cleanse as well as the germicidal and coating actions.

Although research indicates this solution kills the HIV virus (AIDS causing microbe) on contact, three minutes of the oral solution in contact with the mouth is recommended in order to distribute the solution and accomplish a broad spectrum of microbicidal activity. The solution may be combined with a flavoring to make a more palatable toothpaste and/or mouthwash. The active ingredient may also be added to toothpaste, gargle, or breath spray in alternate applications. The active ingredient in the first solution is povidone-iodine, a complex obtained by reacting iodine with the polymer polyvinylpyrrolidone in an oral solution of at least 0.25 percent by weight of povidone-iodine. The active ingredient may be 1-ethenyl-2-pryrrolidinine homopolymer compound with iodine or 1-vinyl-2-pyrrolidone polymers, iodine complex. Concentrations of up to 5.0 percent by weight in the oral solution are also expected to be effective without serious side effects. The remainder of the solution is primarily water, but may also include a buffering compound such as sodium bicarbonate. This solution has been long used for the treatment of sore throats and inflammations of the mouth, but not as a preventive treatment for sexually transmitted diseases. Prior use has shown it to be non-irritating with essentially no significant side effects.

The oral solution can use chlorhexidine gluconate, a salt of chlorhexidine and gluconic acid, as active ingredients, in lieu of povidone-iodine, in a concentration range of 0.08 percent to 0.15 percent per weight. Such a solution is commercially available under the trademark Peridex. Alcohol, glycerin, sodium saccharin and flavoring are added to palatability.

The oral solution can also be prepared using Sodium Propionate as active ingredient in a range of 0.5 percent to 1.5 percent per weight. Such a solution is commercially available under the trademark Prophyllin, a water-soluable powder preparation, that also contains a chlorophyllin agent.

A before-contact body solution is applied to potential exposed skin contact areas, including genitals, up to three (3) hours before sexual contact, including hands, face, lower abdomen, upper thighs and rectum. The preferred embodiment incorporates a water rinse prior to application of the body solution, but an alternate embodiment could use a single application, having the water and/or detergent in the solution serves the entire cleansing purpose. The before-contact body solution can be in the form of a liquid or solid soap, applied while in a shower or while standing in a bath tub. It may also be impregnated into a disposable wash cloth or brush for application. The solution may also be in the form of a gel, aerosol, bath or body oil, to be applied separately or after a rinse or bath. Rinsing with water before and after application of the before-contact solution assists cleaning action, but is not necessary. Even after rinsing, a residue is left on the skin that is resistant to rubbing off (including rubbing off on clothing) and provides up to three (3) hours protection. The method using the preferred embodiment is to rinse the genital area, rectum, lower abdomen, upper inner thighs and around the mouth with water. The sealed port of the single use container of before-contact body solution is manually opened and the liquid contents are poured into the hands, worked into a lather and applied to the genital area, rectal area, lower abdomen, upper inner thighs and around the mouth. The lather is allowed to remain on the body for three (3) minutes to assure full effectiveness. The lathered areas may then be rinsed with water.

The before-contact body solution is a more concentrated solution of povidone-iodine in a sudsing and coating liquid, such as a detergent. It essentially retains the broad microbicidal spectrum of iodine, yet is virtually without undesirable side effects. Again, it has long been used for skin cleansing, including as a douche, to degerm topical skin areas of patients and to help prevent skin infections, but not as part of a sexually transmitted disease prevention method. The skin is wetted with water and sufficient solution added to work up a lather. Although research shows the before-contact body solution kills the HIV virus on contact, retaining the solution in contact with the skin for approximately 3 minutes is recommended to achieve the broad spectrum of microbicidal results. After allowing the lather to remain for approximately these few minutes to optimize microbicidal properties, lather may be rinsed. However, even after rinsing, a major portion of the active ingredient remains on the skin and genital areas.

The body solution is recommended to contain between 7.5 and 10 percent by weight of povidone-iodine, but is also expected to be generally effective in a range of between 2.0 and 12 percent by weight without serious side effects. The remainder of the body solution is primarily water, but again may also contain sodium bicarbonate or other similar compound to control the pH of the solution. An alternate embodiment would have the povidone-iodine complex dissolved in primarily an alcohol solution. The body solution is also expected to be somewhat effective i a concentration as low as 0.25 percent by weight. Although the more concentrated solutions may stain starched linen or clothes, the stain can be washed with soap and water. The solution may also contain flavorings and/or scents, if desired for sensory stimulation. In alternate embodiments, the active ingredient may also be added to soap, perfume, toilet water, wash sponges or cloths, bubble bath, bath oil, bath powder, douche, enemas, towels or towelettes, creams, spermicidal birth control compounds, diaphragms, creams, jellies, aerosols, vaginal sponges and caps, and lotions. These and other products that can come in contact with the exposed skin or orifice areas would contain the added active ingredient of povidone-iodine and may be used in addition to the first and second solutions.

The condom is individually packaged to maintain sterile conditions and is applied to the penis after the hands and penis are cleaned and coated with the before-contact solution. If the hands and/or penis have been exposed to one of the sexual partner's body fluids after application of the solutions but before applications of the condom, additional before-contact solution or after-contact solution (equal in the preferred embodiment) should be applied to the affected areas. The condom should be placed/rolled onto an erect body solution treated penis. The application of the body solution is not expected to affect the birth control effects of the condom and the method may be applied for both purposes.

In pre-intercourse and intercourse activities, fluid exchanges and skin contacts may occur, but all contact areas now have been treated and coated. The preferred embodiment combines the pretreatment cleaning and coating just described, with the proper application and use of a solid barrier as well, such as a condom. Sexual contact may also include the added or combined use of birth control compounds, such as spermicidal creams or other lubricants, vaginal sponges or other implements.

An alternate embodiment comprises the additional solutions and treatments with povidone-iodine of other products and implements that come in contact with exposed skin or orifice areas before or after sexual contact and exposure. This may require changes to the concentration of the two (oral and body) solutions. Concentrations of the active ingredient would be similar to the ranges previously described, but tend to be less concentrated to avoid serious side effects in areas receiving multiple applications of the active ingredient.

After sexual contact, the condom is carefully removed so the penis does not come into contact with the partner's fluids that is present on the condom's exterior, or may be on the testicles, lower abdomen and upper thighs. Careful inspection of the condom for tears and/or leaks is also recommended.

After sexual contact and careful removal of the solid barrier, the after-contact body solution container is opened and liquid is applied as soon as possible after sexual contact. The after-contact application is recommended to be immediately following the sexual contact, but beneficial effect may be achieved up to six hours after the first sexual contact. The genital areas, rectum, lower abdomen, upper thighs an around the mouth are rinsed with water. The individually packaged after-contact body solution is opened and applied to the wet hands and skin, lathered and preferably left standing for three minutes, and rinsed. The same or different flavorings and/or scents may again be added to the solution. The solution destroys microbes on contact, medicates exposed skin areas and also tends to heal or at least coat any new or existing minor irritations and abrasions.

The final process step is to rinse and clean the mouth as soon as possible after sexual exposure with the after-contact oral solution, or similar solution. However, beneficial effect may be achieved by rinsing up to 3 hours after sexual exposure. Again, the same or different flavoring may be added for sensory stimulation. The form may again be a mouthwash, toothpaste, gargle/rinse in one or more packages. In the preferred embodiment, half the contents of the individually packaged after-contact oral solution is applied to the disposable brush and the gums and teeth are brushed. The remaining oral solution is gargled and allowed to remain for three (3) minutes. The gargle/toothpaste is then rinsed. This process cleanses the mouth, throat, kills microbes and provides a coating action against further contamination especially of irritated and abraded areas.

Alternate process steps could comprise applying the before-contact body solution prior to the before-contact oral solution and the after-contact oral solution before the after-contact body solution.

An alternate method using the active ingredient without the before-contact and after-contact applications of the solutions would be to include or apply the povidone-iodine directly to vaginal sponges, condoms, contraceptive foams and jellies, contraceptive creams, aerosols, toilet articles previously described (soap, perfume, toilet water, wash sponges, or cloths, bubble bath, bath oil, bath powder, douche, enemas, towels or towelettes, and lotions) or combined with other products that may contact exposed skin or orifice areas. These products may not serve to cleanse the genital surfaces, but may provide some microbicidal and barrier protections. These other products incorporating povidone-iodine could be used separately and without multiple applications and cleansing solutions. Concentration ranges of the povidone-iodine would be altered from a minimum in these other applications to achieve minimum acceptable microbicidal and barrier properties, to a maximum where no significant adverse side effects were observed in these applications.

It is expected that the preferred embodiment cleaning implements, solutions and method described will be effective against at least 98% of microbes and viruses that are responsible for sexually transmitted disease, including AIDS. The cleansing and sustained microbicial and viricidal barrier and coating of minor cuts/abrasions is expected to last for 3 hours, which appears to be especially important in this application. The cleansing action also eliminates possible environmental contributory factors from the skin and orifices (surface bacteria, fungus, yeast, skin oil, perspiration, etc.).

The invention is now described with reference to an example.

EXAMPLE 1

The effect of the preferred embodiment on the causative microbes of a number of sexually transmitted diseases were researched or tested in the sexual encounter application as previously described. Sexual encounter was/or was expected to be within 3 hours of the first and second applications of the solutions. The solutions were or were assumed to be in contact for a minimum of approximately two (oral) or three (skin) minutes prior to discharge or rinsing. The solutions used or analyzed were essentially as previously described. Table 1 lists the results of the research/testing.

TABLE 1

| DISEASE | CAUSATIVE MICROBES | MICROBICIDAL EFFECT |
|---------|--------------------|--------------------|
| Coliforms | Escherichia coli, Aeromonas, Enterobacters, Campylobacters, Shigella, Proteus Salmonella, and Pseudomonas | positive |
| AIDS | HIV | positive |
| Herpes | Herpes Simplex I & II | positive |
| Cytomegalovirus | Cytomegalo virus | positive |
| Syphilis | Treponema Pallidum | positive |
| Tricomonas | Trichomonas vaginalis | positive |
| Entamoeba | Entamoeba histolytica | positive |
| Mycoplasma | Mycoplasma hominis | positive |
| Gardnerelia | Gardnerelia vaginalis | positive |
| Cornynevacterium vaginalis | Gardnerelia vaginalis | positive |
| Haemophilis vaginalis | Gardnerelis vaginalis | positive |
| Ureaplasma | Ureaplasma urealyticum | positive |
| Chlymedia | Chlymedia trachomatis | positive |
| Gonorrhea | Neisseria gonorrhea | positive |
| Candidiasis | Candida allbicans | positive |
| Strept. infections | Streptococcus faecalis | positive |
| Staph. infections | Staphyloccus aureus | positive |
| Group A & B | Streptococcus -beta hemolytic (group A & B) | positive |
| Lymphogranuloma venereum | Chylmedia trachomatis | positive |

While the preferred embodiments of the invention have been described, modifications can be made and other embodiments may be devised without departing from the spirit of the invention and the scope of the appended claims.

What is claimed is:

1. A prophylactic kit for use in connection with sexual intercourse and related intimate contacts between partners, which comprises:
   a sealed enclosure, and therein:
      a condom;
      a first container holding a quantity of a first liquid solution of povidone-iodine;
      a second container holding a quantity of a second liquid solution of a microbicidal agent taken from a group consisting of povidone-iodine, chlorhexidine gluconate and sodium propionate;
   wherein said first solution is formulated for topical applications, and said second solution is formulated for use as a mouthwash; and
   written indications and instructions for use of the kit before and after said sexual intercourse and related intimate contacts.

2. The kit claimed in claim 1, wherein:
   said first solution contains between 2 and 12 percent by weight of povidone-iodine; and
   said second solution contains between 0.25 percent and 5 percent per weight of povidone-iodine.

3. The kit claimed in claim 2 which further comprises:
   a third container holding a quantity of said first solution; and
   a fourth container holding a quantity of said second solution;
   wherein said first and second containers are marked for use before sexual intercourse; and
   said third and fourth containers are marked for use after sexual intercourse.

4. The kit claimed in claim 3 which further includes at least one toothbrush within said sealed enclosure.

5. The kit claimed in claim 3, wherein said first solution contains a detergent.

6. The combination as claimed in claim 3, wherein said solutions are in a generally liquid form.

7. The kit claimed in claim 1, wherein said second solution contains between 0.08 percent and 0.15 percent per weight of chlorhexidine gluconate.

8. The kit claimed in claim 1, wherein second solution contains between 0.5 percent and 1.5 percent per weight of sodium propionate.

* * * * *